United States Patent [19]

Ishiguro

[11] Patent Number: 4,738,920
[45] Date of Patent: Apr. 19, 1988

[54] METHOD FOR ASSAYING A BIOCOMPONENT USING 4-METHOXY-1-NAPHTHOL AND HYDROGEN PEROXIDE

[75] Inventor: Tatsuya Ishiguro, Kyoto, Japan

[73] Assignee: Kyowa Medex Co., Ltd., Tokyo, Japan

[21] Appl. No.: 748,050

[22] Filed: Jun. 24, 1985

[30] Foreign Application Priority Data

Jun. 26, 1984 [JP] Japan .................. 59-131556

[51] Int. Cl.$^4$ .................. G01N 33/561; G01N 33/535
[52] U.S. Cl. .......................................... 435/6; 435/7; 435/28; 435/805; 436/516; 436/904
[58] Field of Search .................. 435/7, 28, 805, 6; 436/516, 904

[56] References Cited

U.S. PATENT DOCUMENTS

| | | | |
|---|---|---|---|
| 3,983,005 | 9/1976 | Goodhue | 435/11 |
| 4,200,508 | 4/1980 | Hirai | 436/516 |
| 4,235,960 | 11/1980 | Sasse | 435/7 |
| 4,272,504 | 6/1981 | Kim | 436/531 |
| 4,446,240 | 5/1984 | Nerenberg | 436/544 |

OTHER PUBLICATIONS

Taketa Electrophoresis 1983, 4, pp. 371–373.

*Primary Examiner*—Robert J. Warden
*Assistant Examiner*—Robert Benson
*Attorney, Agent, or Firm*—M. N. Meller

[57] ABSTRACT

The present invention provides a method for assaying a biocomponent on the basis of an amount of bound peroxidase by the steps of supporting a biocomponent or a target substance containing a biocomponent on a gel-like carrier, developing the biocomponent or the target substance by electrophoresis, binding a receptor to the biocomponent or the target substance, binding peroxidase to the receptor, and determining the amount of the bound peroxidase, wherein hydrogen peroxide and 4-methoxy-1-naphthol are used as substrates.

6 Claims, 2 Drawing Sheets

METHOD FOR ASSAYING A BIOCOMPONENT USING 4-METHOXY-1-NAPHTHOL AND HYDROGEN PEROXIDE

BACKGROUND OF THE INVENTION

1. Field of Invention

This invention relates to an improvement in an assaying method as used in the immuno-serologically and pathologico-histologically qualitative and quantitative determination of a biocomponent, and to a method for diagnosing cancer according to the assaying method.

2. Prior Art

The following methods have been known so far for detection of a biocomponent, for example, serum protein: coloring matter-staining method, silver stain method, autoradiographical method, immunological method using a labelled antibody, for example, enzyme immunoassay (EIA), fluoroimmunoassay (FIA), radioimmunoassay (RIA), etc. As the enzyme immunoassay, the method of Takeda, et al. is known (Electrophoresis 1983, 4, 371-373). Diagnosis of cancer has been carried out so far according to these methods.

The coloring matter-staining method is high in background, unclear, and poor in detection sensitivity.

The silver stain method and the autoradiographical method are high in sensitivity and accuracy, but complicated in operational procedures, and cannot be carried out promptly and simply. On account of using heavy metals and isotopes, they have a waste disposal problem, and furthermore their measurement items are limited, so that they have no wide application.

The immunological methods can specifically detect a single substance, and have a very high measuring sensitivity, a distinguished quantitative determination and a wide application. However, the radioimmunoassay has problems in radiation exposure, handling control, waste disposal, etc. owing to the use of radioisotopes. The fluoroimmunoassay has a complicated operational procedure and no applicability to double staining and thus has a limited application. It is said that the enzyme immunoassay generally has a high detecting sensitivity and is clear and comparatively simple and rapid in operational procedures. However, the conventional method for coloring in a gel-like carrier, using an enzyme-labelled antibody has problems of high background, uncleanness, low sensitivity, etc.

When biocomponents are supported on a gel-like carrier or a carrier membrane and developed by electrophoresis, the control marker for the migration is generally made to migrate apart from the biocomponents but in parallel to the biocomponents. This method has problems such as poor reproducibility of migration distances of biocomponents, low accuracy in measurements, etc.

A method for applying the enzyme immunoassay to a coloring system in a gel-like carrier has been little known, and no thorough studies have been made of optimum conditions for the reaction, that is, combinations with an enzyme, a substrate, etc. of a receptor capable of being specifically bound to a target substance.

SUMMARY OF THE INVENTION

Taking into account those regarded as specific reactions in the biological phenomena, for example, specific reaction of an antigen with an antibody, of an enzyme with a substrate, of an enzyme with a coenzyme, of avidin with biotin, of a hormone with a receptor, lectin and special sugar combination, complementation of nucleic acid (for example, poly U and poly A, etc.), specifically bound protein (for example, B-2 protein-bound protein, C-reactive protein, etc.), protein A and IgG molecules, etc., the present inventor has made a study of assaying biocomponents, and has found that biocomponents can be quantitatively determined clearly, simply and rapidly with a high sensitivity when hydrogen peroxide and 4-methoxy-1-naphthol are used as substrates in a method for assaying the biocomponents, where the detection of products from these reactions is carried out in a gel-like carrier, on the basis of an amount of bound peroxidase by utilizing bonding of (a) a biocomponent or a target substance containing a biocomponent, (b) a receptor capable of being specifically bound to the biocomponent or to the target substance containing the biocomponent, and (c) peroxidase (POD).

The aforesaid method of Takeda, et al. discloses use of 4-chloro-1-naphthol, whereas the present method uses 4-methoxy-1-naphthol. The present method differs from the method of Takeda, et al. in this respect, and is remarkably distinguished therefrom in the effects, for example much shortened coloring time and migration time, clearer migration diagram, and higher assay sensitivity and resolving power at least by one figure.

When the biocomponents are quantitatively determined by electrophoresis, no control marker for the migration is made to migrate in parallel in contrast to the conventional method, but a control marker combined with a coloring matter such as Bromophenol Blue, etc. is mixed with the biocomponents, and made to migrate together, whereby the reproducibility of migration distance and the accuracy of measurements can be made considerably higher than those of the conventional method.

DETAILED DESCRIPTION

Figure 1:
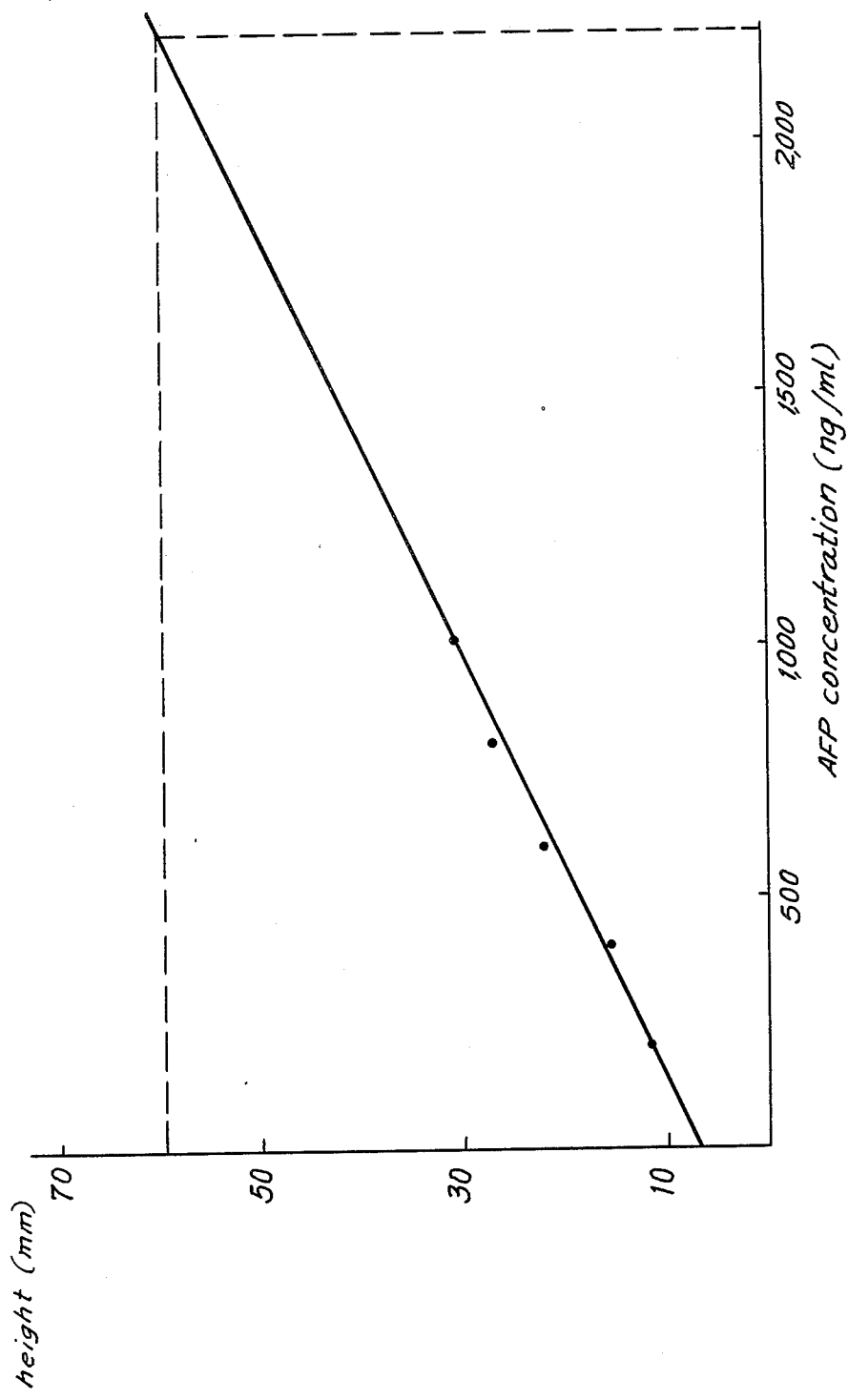
FIG. 1 shows a standard curve in AFP standard serum assay in Example 1.

The present invention relates to a method for assaying a biocomponent on the basis of an amount of bound peroxidase by utilizing bonding of a biocomponent or a target substance containing a biocomponent, a receptor capable of being specifically bound to the biocomponent or the target substance containing the biocomponent, and peroxidase, wherein hydrogen peroxide and 4-methoxy-1-naphthol are used as substrates.

The biocomponent assayable in the present invention includes antigen, antibody, enzyme, substrate for enzyme, coenzyme, protein, glycoprotein, glucide, glycolipid, lipoprotein, nucleic acid, hormone, etc., which usually exist in various body fluids, pathological tissue section, etc.

The various body fluids include, for example, blood, urine, saliva, gastric juice, intestinal juice, pancreatic juice, bile, tissue fluid, edema fluid, ascitic fluid, hydrothorax fluid, hydropericardic fluid, synovial fluid, cerebrospinal fluid, amniotic fluid, genital secretion fluid, mother's milk, nasal mucus, phlegm, tear, sweat, vitreous body, etc., and it is particularly preferable to use blood in the form of serum or plasma.

The target substance means a substance wherein a biocomponent and a label compound are linked and the label compound includes an antigen, antibody, enzyme, substrate for enzyme, coenzyme, protein, glycoprotein, glucide, glycolipid, lipoprotein, nucleic acid, hormone, avidin, biotin, etc.

The receptor includes an antibody, protein A, enzyme, substrate for enzyme, coenzyme, nucleic acid, hormone-receptor, specifically bound protein (B-2 protein-bound protein, C-reactive protein, etc.), avidin, biotin, lectin, etc.

The present method is applicable to the ordinary enzyme immunoassays, and particularly useful for assaying a biocomponent supported on a gel-like carrier. Particularly excellent is a method using protein A as a receptor, peroxidase as enzyme and hydrogen peroxide and 4-methoxy-1-naphthol as substrates.

Since the assaying conditions such as the amount of assay sample, the amount and the ratio of enzyme-labelled receptor, the amount of substrate, reaction time and temperature, etc. depend on the kind of substance to be assayed, the titer of receptor to be used, the kind of carrier, etc., the most suitable conditions must be selected for each assay sample.

For example, when labelled protein is used in staining after gel electrophoresis, an elimination of unbound substance is carried out after the gel electrophoresis, and then a predetermined amount of POD-labelled protein A is added dropwise to the gel surface, followed by allowing the assay sample to stand approximately at room temperature, preferably at 15° to 25° C. for 30 to 45 minutes. Then, the assay sample is washed with an appropriate buffer solution for 30 to 40 minutes, and then 4-methoxy-1-naphthol is added thereto to conduct an enzyme reaction.

After the precipitate line is thoroughly colored (usually a reaction takes place for 2 to 3 minutes), the assay sample is washed and decolorized to wash out the unreacted substances and the reaction is discontinued. In the washing and decolorization, an appropriate reagent may be used, but it is preferable in view of simplicity and rapidity to use running water. Rapid drying makes gel drying uneven, making the surface rough and causing the assay to be interfered with. Thus, it is preferable to carry out drying at a temperature from room temperature to 60° C. Even a permanent preservation can be made by preventing breakage.

It is preferable to adjust the concentration of POD-labelled protein A to 0.01 to 0.5% (W/V) by an appropriate dilute solution, and the preferred dilute solution is a barbital buffer solution at a pH of about 8.6. The preferred NaCl concentration of the barbital buffer solution is 0.05 to 0.5M. The coloring reagent solution is a solution of about 1% 4-methoxy-1-naphthol in an appropriate solvent, which is further diluted to 0.001 to 0.1% when used. The preferred dilute solution is a Tris-hydrochloric acid buffer solution at a pH of about 7.0 to 8.5. The method for preparing a gel-like carrier is not particularly limited, and any conventional method can be used. For example, a predetermined amount of agar, agarose or the like is added to a dilute solution such as distilled water, a barbital buffer solution at a pH of about 8.6 or a Tris-hydrochloric acid buffer solution, and heated at a temperature from 60° to 80° C. with gentle stirring to make a solution, and then the solution is made to flow on a desired flat plate, left for cooling, and coagulated in a gel state.

The concentration of gel can be selected in view of the sizes (molecular weights, configurations, etc.) of the biocomponent (target substance)-labelled receptor combination and reaction product (coloring matter). The gel concentration is usually 0.5 to 2.0% (W/V), preferably 0.8 to 1.0% (W/V), and if necessary, an antiseptic may be added thereto.

The present invention is useful for assaying a biocomponent supported on a carrier membrane besides the gel-like carrier, and the carrier membrane includes, for example, a nitrocellulose membrane, cellulose-acetate membrane, acetate membrane, etc. The present invention is also applicable to immuno-histochemical staining of tissue sections as used in the fields of histochemistry and cytochemistry.

When the biocomponent in a body fluid is quantitatively determined by electrophoresis, coloring matter-bound albumin is usually migrated in parallel as a control marker for the migration. In the conventional method, the migration conditions are usually liable to differ between the control marker and the biocomponent due to a local structural deformation of the gel, unevenness in the gel structure, electrical load conditions, temperature difference, etc., resulting in poor reproducibility. There is also a problem in the accuracy of measurement values.

The present inventor has found that measurement values having better accuracy and reproducibility than those of the conventional method can be obtained by using a protein having a different antigen specificity from that of the biocomponent as an internal standard substance, and adding to the carrier a receptor capable of being specifically bound to the internal standard substance.

That is, when a mixture of the internal standard substance colored by a coloring matter (for example, Bromophenol Blue, which will be hereinafter referred to as BPB) with a body fluid is subjected to electrophoresis on a gel-like carrier containing an antibody against the biocomponent and the internal standard substance, measurement values having better accuracy and reproducibility can be obtained.

As the internal standard substance to be usable in the present invention, a substance having no cross reaction with the biocomponent is employed. Such protein includes human serum albumin, bovine serum albumin, egg albumin, chick serum albumin, etc. Particularly preferred are egg albumin and chick serum albumin.

As the receptor, a monoclonal or polyclonal antibody against these albumins can be used.

The coloring matter for coloring the internal standard substance includes Bromophenol Blue, Bromothymol Blue, etc. To avoid tailing by a non-bonding type coloring matter during the migration, it is preferable to adjust the concentrations of these coloring matters to 0.001 to 0.1% (W/V).

In the method of the present invention, a coloring matter, internal standard substance, and body fluid are directly mixed with one another, or a mixture of the coloring matter and the internal standard substance is smeared onto a flat plate for reaction, and dried, and then the body fluid is added dropwise to the flat plate and mixed.

The latter procedure is preferable, because of no influence of the biocomponent concentration in the body fluid, good preserving stability of the internal standard substance, and simple and rapid operation.

The present invention is described in detail below, referring to Examples, but the scope of the present invention is not restricted by the following Examples.

EXAMPLE 1

Investigation of quantitative determinability by rocket electrophoresis:

(a) Preparation of AFP standard serum:

AFP standard serum (1041 ng/ml, made by DAKO Co., Denmark) was diluted with normal human serum (AFP: 5 ng/ml or less) to prepare AFP standard serums (100, 200, 400, 600 and 800 ng/ml).

(b) Preparation of anti-AFP-containing agarose plate:

At first, 20 µl of anti-AFP serum (made by DAKO Co.) was added to 10 ml of 1.0% agarose (dissolved in a barbital buffer solution having a pH of 8.6 and an ionic strength of 0.05, made by FMC Marine Colloids Division Co., U.S.A.) and mixed. The anti-AFP serum-containing agarose gel was poured into a gel bond (110×125 mm, made by FMC Marine Colloids Division Co.) and coagulated to prepare an anti-AFP-containing agarose plate having a thickness of about 1 mm.

(c) Preparation of POD-labelled protein A dilute solution:

To 20 µl of POD-labelled protein A (made by E. Y. Laboratories, U.S.A.) was added 10 ml of a dilute solution (prepared by dissolving 14.0 g of NaCl in 1 l of barbital buffer solution having a pH of 8.6) to make a 0.2% POD-labelled protein A dilute solution.

(d) Preparation of reagent solution for coloring:

Just before application, 200 µl of 4-methoxy-1-naphthol (made by Aldrich Co., U.S.A.), 10 ml of 0.05M Tris-hydrochloric acid buffer solution (solution made by mixing trishydroxymethylaminomethane at 12.114 g/l and 0.1M HCl in a ratio of 100:77, pH 7.6) and a drop of 30% $H_2O_2$ were mixed together to make a reagent solution for coloring.

(e) Measurement of AFP:

At first, 10 µl each of the AFP standard serums (100, 200, 400, 600, and 800 ng/ml) obtained in said section (a) were poured into holes (4.0 mm in diameter) on the anti-AFP-containing agarose plate prepared in said section (b), and subjected to electrophoresis at 3 mA/cm for 90 minutes with cooling at 10° C. After the migration, the plate was treated with an absorbent pad (made by Nihon Shoji Co., Japan) for 2 to 3 minutes for elimination of unbound substances, and then washed with a phosphate buffer solution (pH 7.2) for 30 minutes. Then, the plate was dried again with an absorbent pad, and 10 ml of the POD-labelled protein A prepared in said section (c) was poured onto the flat plate. After the reaction had proceeded for 30 minutes, the steps of drying with the absorbent pad, washing with the phosphate buffer solution (pH 7.2) for 30 minutes and drying with the absorbent pad were repeated in the same manner as above, and the 10 ml of the reagent solution for coloring prepared in said section (d) was added to the plate and then the reaction was carried out for 2 to 3 minutes. After water washing for 2 to 3 minutes, the plate was dried with an absorbent pad and the heights of precipitate lines were measured. The thus obtained standard curve is shown in FIG. 1.

EXAMPLE 2

Measurement of AFP in amniotic fluid by Concanavalin-A (which will be hereinafter referred to as "Con-A", made by Pharmacia Fine Chemicals Inc., Sweden)-adsorption cross-immunoelectrophoresis (CAIE):

(a) Preparation of assay sample:

Amniotic fluids collected from 16 pregnant women of pregnancy of from 7 to 18 weeks were centrifuged (3,000 rpm for 20 minutes) and $NaN_3$ was added to the supernatants to a concentration of about 0.001% (W/V). The mixtures were freezedried at −20° C. to make assay samples.

(b) Preparation of Con-A-containing agarose plate (for one-dimensional migration):

To 10 ml of 1.0% agarose (dissolved in a barbital buffer solution having a pH of 8.6 and an ionic strength of 0.05) was added 600 µg/ml of Con-A. Then, 15 ml of the Con-A-containing agarose gel was poured onto a gel bond (110×125 mm, made by FMC Marine Colloids Division Co.) and coagulated to make a Con-A-containing agarose plate having a thickness of about 1 mm.

(c) Measurement of AFP:

At first, 10 µl of the sample prepared in said section (a) was poured into holes (4 mm in diameter) on the Con-A-containing agarose plate prepared in said section (b), and subjected to one-dimensional electrophoresis. Migration was carried out with a barbital buffer solution (pH 8.6 at 3 mA/cm for 90 minutes with cooling at 10° C.

As a control, 5 µl of 3% (W/V) human serum albumin [fraction V, made by Sigma Co., U.S.A., containing 0.01% (W/V) BPB] was used and the about 6 cm-migrated position was marked.

After the one-dimensional electrophoresis, the agarose plate was cut off with a width of about 1 cm in parallel to the migrating direction, and tightly placed on the anti-AFP-containing agarose plate prepared in Example 1, section (b), and subjected to two-dimensional electrophoresis in the direction perpendicular to the direction of one-dimensional development at 2.5 mA/cm for 2 hours with cooling at 10° C.

After the migration, the plate was treated with an absorbent pad (made by Nihon Shoji Co., Japan) for 2 to 3 minutes, for elimination of unbound substances, and then washed with a phosphate buffer solution (pH 7.2) for 30 minutes. Again, the plate was dried with an absorbent pad, and 10 ml of POD-labelled protein A prepared in Example 1, section (c), was poured onto the flat plate. After the reaction had proceeded for 30 minutes, the steps of drying with an absorbent pad, washing with a phosphate buffer solution (pH 7.2) for 30 minutes and drying with an absorbent pad were repeated in the same manner as above, and then 10 ml of the coloring reagent solution prepared in Example 1, section (d) was added thereto. The plate was subjected to reaction for 2 to 3 minutes. After washing with water for 2 to 3 minutes and drying with an absorbent pad, the distance from the albumin position obtained in the one-dimensional electrophoresis to a migration peak shown in the two-dimensional electrophoresis was measured.

Figure 2:
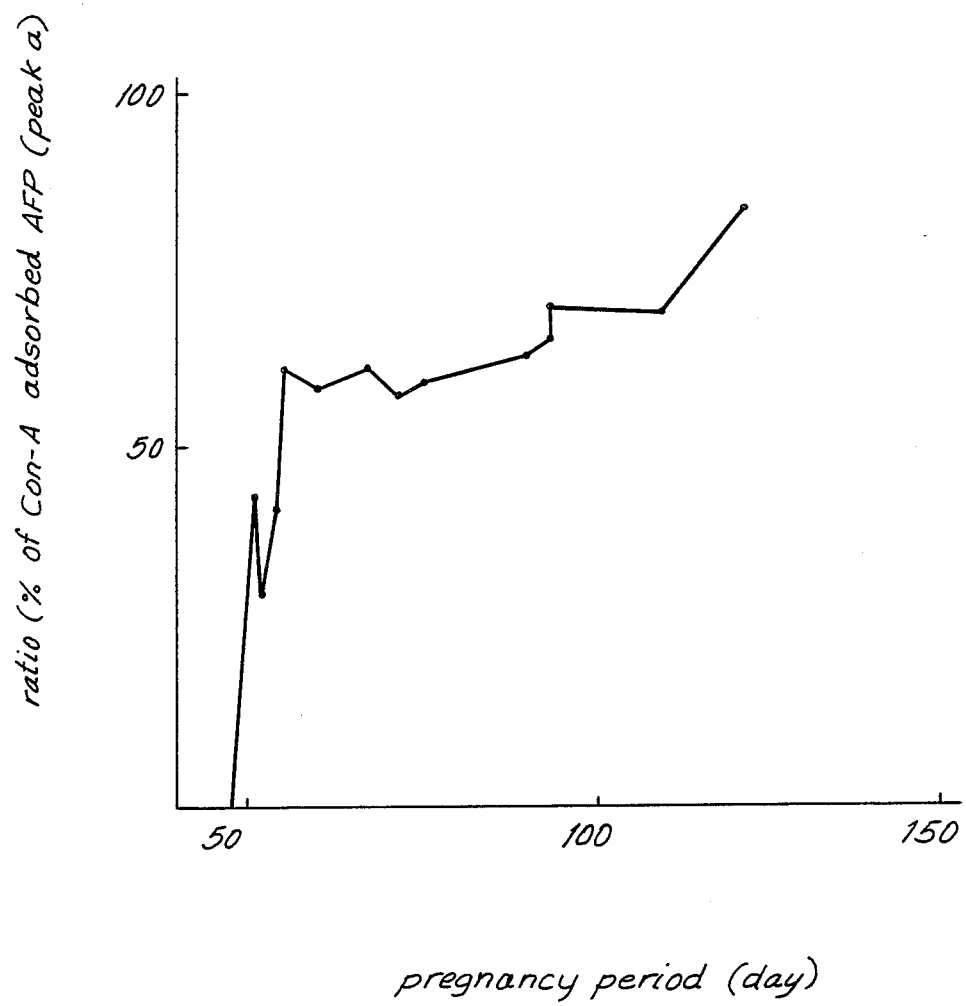
FIG. 2 shows the result of AFP measurement in amniotic fluids in Example 2.

AFP in the amniotic fluid is divided into two fractions by means by Con-A-CAIE. The fraction having an immune precipitate peak at the AFP-migrated position on the lectin-free agarose flat plate by one-dimensional electrophoresis is Con-A unadsorbed AFP (peak b), whereas the peak shown on the cathode side therefrom is Con-A-adsorbed AFP (peak a). FIG. 2 shows a graph on which proportions of peaks b are plotted with changes in pregnancy period, defining the total height of peaks a and b as 100%. That is, FIG. 2 shows that the Con-A adsorbed AFP in the amniotic fluid tends to increase with the elapse of time.

EXAMPLE 3

Measurement of AFP in the serum of patients suffering from hepatic carcinoma by Con-A-CAIE (a) Preparation of assay sample:

Serums of 47 cases of primary hepatic carcinoma and 8 cases of metastatic hepatic carcinoma were diluted with normal human serum (AFP: 5 ng/ml or less) to prepare assay samples having not more than 15,000 ng/ml of AFP.

(b) Measurement of AFP:

Measurement was carried out in the same manner as in Example 2.

As a result, typical migration patterns of serums of patients suffering from hepatic carcinoma by Con-A-CAIE are classified into the type in which a single peak a appears (Type 1), the type in which two fractions, peaks a and b appear (Type 2), and the type in which a single peak b appears (Type 3). As shown in Tables 1 and 2, the AFP in the serum of primary hepatic carcinoma can be divided into Type 1 (single peak a) and Type 2 (peak a>peak b), whereas that in the metastatic hepatic carcinoma can be divided into Type 2 (peak a<peak b) and Type 3 (single peak b), and thus, this is useful for the differential diagnosis of cancer.

TABLE 1

| AFP fraction appearance frequency by Con-A-CAIE | | | |
|---|---|---|---|
| Fraction pattern | Fraction as appeared | Primary hepatic carcinoma | Metastatic hepatic carcinoma |
| Type 1 | a | 29 (61.7%) | 0 |
| Type 2 | a, b | 18*(38.3%) | 6 (75%) |
| Type 3 | b | 0 | 2 (25%) |
| | | 47 | 8 |

*At least two measurements were made for each case, and every case where Type 2 appeared in at least one measurement was classified into Type 2.

TABLE 2

| Height of peak b and kind of hepatic carcinoma in Type 2 by Con-A-CAIE | | |
|---|---|---|
| | Primary hepatic carcinoma | Metastatic hepatic carcinoma |
| Number of investigation | 18 | 6 |
| Height at peak b | | |
| Average % | 14.1 ± 3.6*[1] | 44.5 ± 20.2*[2] |
| Range | 8–22 | 17–68 |

*[1]The higher value was adopted where several measurements were made for each case.
*[2]The lower value was adopted where several measurements were made for each case.

EXAMPLE 4

Procedure for measuring AFP in serum of cancer patient by using chick serum albumin (fraction V, made by Sigma Co., U.S.A.) as an internal standard substance:

(a) Preparation of assay sample:

BPB (made by Sigma Co.) was prepared at 0.005% (W/V) with 0.0025% (W/V) chick serum albumin, and then 10 µl of the preparation was smeared onto a plate and dried. A drop (25 µl) of serum of a patient suffering from hepatic carcinoma was added to the plate through a Pastem pipette to make an assay sample.

(b) Preparation of lentyl lectin (which will be hereinafter referred to as LCH, made by Pharmacia Fine Chemicals Inc.)-containing agarose plate (for one-dimensional migration):

A plate was prepared in the same manner as in Example 2, section (b) except that LCH was added to 1.0% agarose in place of Con-A of Example 2, section (b) to a final concentration of 200 µg/ml.

(c) Preparation of agarose plate for two-dimensional migration:

A plate was prepared according to Example 1, section (b), except that 20 µl of anti-AFP serum (made by DAKO Co.) and 10 µl of anti-chick serum albumin serum (made by Cappel Co., U.S.A.) were added to 10 ml of 1.0% agarose.

(d) Measurement of AFP:

At first, 10 µl of the assay sample prepared in said section (a) was poured into holes on the LCH-containing agarose plate prepared in said section (b) and subjected to one-dimensional electrophoresis under the same conditions as in Example 2, section (c), and the position of BPB marker was marked after the migration.

Then, the agarose plate was cut off in parallel to the migrating direction, tightly placed on the agarose plate prepared is said section (c), subjected to two-dimensional electrophoresis under the same conditions as in Example 2, section (c), and colored. Distances to the respective migration peaks from the position of chick serum albumin precipitate peak as the point of origin were measured.

The precipitate peak of chick serum albumin was not crossed with the precipitate peak of serum of a patient suffering from hepatic carcinoma, and formed at the substantially same position as that of BPB marker after the one-dimensional migration.

Effects of the Invention

According to the present invention, biocomponent assaying can be carried out on a lower background, with a higher clearness, sensitivity, rapidity, simplicity, reproducibility and accuracy than those of the conventional methods. Particularly in a color-developing system in a gel-like carrier, the measurement sensitivity is about 20-times higher, for example, from 2,000 ng/ml to about 100 ng/ml. The present invention is well applicable to screening. Furthermore, higher reproducibility and accuracy can be attained by introduction of an internal standard system. Generally, when the reaction time is shortened, there is a problem of decrease in the measurement sensitivity and accuracy, whereas in the present invention the measurement time can be considerably shortened, with a considerable increase in measurement sensitivity and accuracy.

For example, in the case of Con-A-CAIE of Example 2, the two-dimensional migration time, which usually takes 16 hours in protein staining, can be reduced to 2 hours. Also, the coloring time, which takes 30 minutes to one hour according to the conventional method, can be reduced to only 2 to 3 minutes. Furthermore, the antibody concentration during the two-dimensional migration can be enough at 0.15 to 0.3% owing to the increased sensitivity.

Furthermore, the stained product of the present invention undergoes no fading, and thus the data can be permanently preserved. This is a great advantage.

According to the present invention, all the substances assayable by the conventional enzyme immunoassay can be also assayable, and the present invention has an important significance particularly in the diagnosis of cancer, judgement of curing effects, etc. owing to its distinctiveness in not only the qualitative, but also the quantitative determination.

I claim:

1. In an immunoelectrophoresis method for assaying a biocomponent on the basis of an amount of bound peroxidase by the steps of spotting a gel-like carrier with drops of a biocomponent or a target substance containing a biocomponent, developing the biocomponent or the target substance by electrophoresis, binding a receptor-peroxidase conjugate to the biocomponent or to the target substance washing away the unbound receptor-peroxidase conjugate and determining the amount of bound peroxidase, the improvement comprising the use of hydrogen peroxide and 4-methoxy-1-naphthol as substrates.

2. The method according to claim 1, wherein the biocomponent is selected from the group consisting of antigens, antibodies, substrates for enzymes, coenzymes, proteins, glycoproteins, glucides, glycolipids, lipoproteins, and nucleic acids.

3. The method according to claim 1, wherein the target substance is a substance wherein a biocomponent and a label compound are linked and the label compound is selected from the group consisting of antigens, antibodies, substrates for enzymes, coenzymes, proteins, glycoproteins, glucides, glycolipids, lipoproteins, nucleic acids, avidin and biotin.

4. The method according to claim 2, wherein the glycoprotein is selected from the group consisting of $\alpha$-fetoprotein (AFP), human chorionic gonadotropin (HCG), $\gamma$-glutamyltransferase ($\gamma$-GTP) and carcinoembryonic antigen (CEA).

5. The method according to claim 1, wherein the receptor is selected from the group consisting of antibodies, protein A, enzymes, substrates for enzymes, coenzymes, nucleic acids, specifically bound proteins, avidin, biotin and lectin.

6. a method for diagnosing cancer, detectable by the presence of AFP using the assaying method according to claim 1.

* * * * *